United States Patent [19]

Mull

[11] Patent Number: 5,122,152
[45] Date of Patent: Jun. 16, 1992

[54] SUTURE REMOVING DEVICE

[76] Inventor: John D. Mull, 4088 Lakeshore Rd., Burlington, Ontario, Canada, L7L 1A1

[21] Appl. No.: 314,737

[22] Filed: Feb. 24, 1989

[51] Int. Cl.$^5$ .............. A61B 17/00; B26B 3/00; B25F 3/00
[52] U.S. Cl. .................... 606/170; 606/167; 30/124; 30/134; 30/129; 30/DIG. 8; 30/294
[58] Field of Search .............. 128/305, 318, 334 R; 30/134, DIG. 8, 124, 320, 254, 294, 129; 606/167, 170

[56] References Cited

U.S. PATENT DOCUMENTS

| | | | |
|---|---|---|---|
| 2,696,621 | 12/1954 | Miller | 30/DIG 8 |
| 2,865,099 | 12/1958 | Blackwood | 30/134 |
| 3,266,493 | 8/1966 | Cummings | 128/318 |
| 3,802,074 | 4/1974 | Hoppe | 30/134 |
| 3,879,846 | 4/1975 | Allen, Jr. | 128/354 |
| 4,034,473 | 7/1977 | May | 128/318 |
| 4,053,979 | 10/1977 | Tuthill et al. | 30/124 |
| 4,271,838 | 6/1981 | Lasner et al. | 128/318 |
| 4,432,138 | 2/1984 | Piccolo, Jr. | 30/DIG. 8 |
| 4,473,076 | 9/1984 | Williams et al. | 128/305 |
| 4,494,542 | 1/1985 | Lee | 128/305 |
| 4,709,481 | 12/1987 | Moore | 128/305 |
| 4,753,009 | 6/1988 | Haga | 30/254 |

Primary Examiner—Stephen C. Pellegrino
Assistant Examiner—Gary Jackson
Attorney, Agent, or Firm—Bereskin & Parr

[57] ABSTRACT

There is described a suture removing device comprising a body having a handle portion, a head portion, and a cutting edge provided in the head portion. The head portion has a leading end with a forked tip and a surface extending rearwardly of the tip to the cutting edge. The forked tip is inserted below a suture to lift the suture from the skin and pushed forwards such that the suture rides along the surface and on to the cutting edge where the suture is cut. The forked tip of the device is then placed around the suture, below the suture knot, to allow the suture to be pulled out.

9 Claims, 2 Drawing Sheets

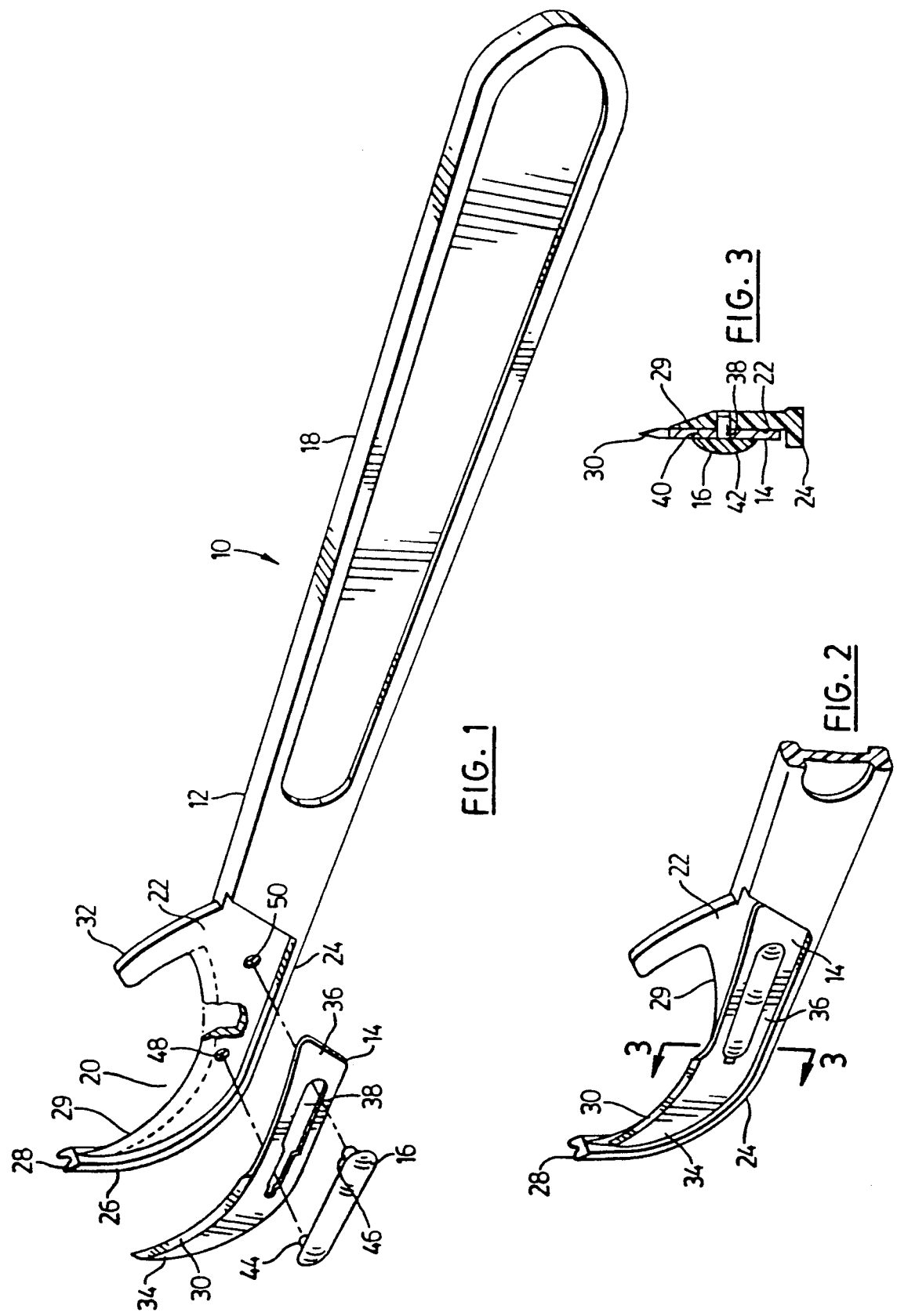

SUTURE REMOVING DEVICE

FIELD OF THE INVENTION

This invention relates to a suture removing device.

In the practise of medicine sutures are used frequently to unite the edges of wounds resulting from surgery or accidental injury. The sutures are normally removed when the wound has healed sufficiently to remain closed without the aid of the sutures.

At present, doctors remove sutures by means of tweezers and a scalpel or scissors. The tweezers are used to lift the suture from the skin and the suture is then cut with the scalpel or scissors. The doctor then has to grasp the knot of the suture with the tweezers and remove the suture. If a scalpel is used to cut the suture, great care must be taken to prevent the exposed blade accidentally nicking the skin of the patient, whereas scissors, though easier to use, are often dull.

The tweezers and scalpel or scissors are conventionally provided as part of a kit comprising a sterile pack containing a tray carrying the instruments. Clearly, before a doctor can remove a suture such a kit must be located. As the kits are fairly bulky they will often be located in storage areas and a member of staff must be sent to retrieve a kit. This is time consuming and in a busy hospital there will not always be the necessary manpower available to fetch a kit when required. After use, the kit has to be returned for sterilization.

SUMMARY OF THE PRESENT INVENTION

According to one aspect of the present invention there is provided a suture removing device comprising a body having a handle portion, a head portion, and a cutting edge provided in the head portion. The head portion has a leading end with a forked tip and a surface extending rearwardly of the tip to the cutting edge.

According to a further aspect of the present invention there is provided a method of removing a knotted suture from the body of a patient comprising: providing a suture removing device comprising a handle portion, a head portion and a cutting edge provided in the head portion, the head portion having a leading end with a forked tip and a surface extending rearwardly of the tip to a cutting edge; inserting the forked tip of the device below a suture to lift the suture from the skin; pushing the device forwards such that the suture rides along the surface and onto the cutting edge to cut the suture; and placing the forked tip of the device around the suture below the suture knot and pulling out the suture.

BRIEF DESCRIPTION OF THE DRAWINGS

These and other aspects of the present invention will now be described, by way of example, with reference to the accompanying drawings, in which:

FIG. 1 is an exploded and partially cut away perspective view of a suture removing device in accordance with a preferred embodiment of the present invention;

FIG. 2 is a perspective view of the head portion of the device of FIG. 1 shown assembled;

FIG. 3 is a sectional view on line 3—3 of FIG. 2; and

DESCRIPTION OF THE PREFERRED EMBODIMENT

Figure 4:
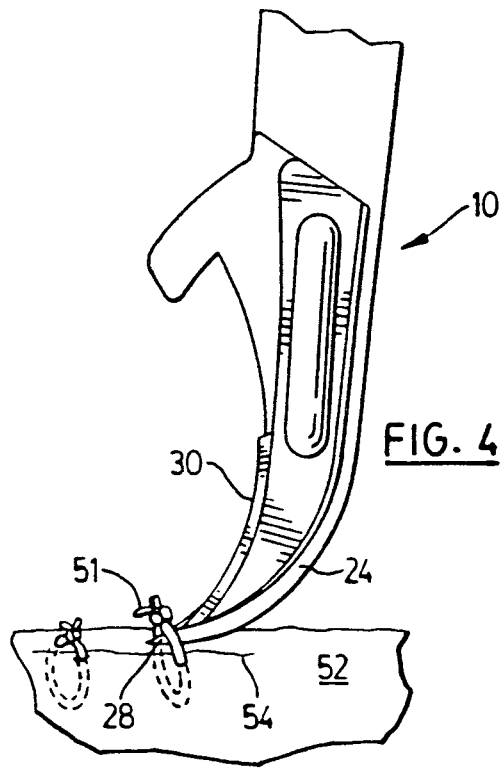
FIGS. 4 to 6 are views of a suture removal operation carried out using the device of FIG. 1.

Reference is first made to FIG. 1 of the drawings which shows a suture removing device 10 comprising an elongate body 12, a removable blade 14 and a blade retainer 16 for securing the blade to the body. The body 12 is formed of a plastic molding and comprises a handle 18 shaped to be comfortably gripped by a user's hand and a head 20 which holds the blade 14.

The head 20 has a recessed portion 22 to accommodate the blade 14 bordered by a rib 24 which initially extends straight from the handle portion 18 and then curves inwardly at 26 to terminate at a forked tip 28. The rear edge of the blade 14 is of complementary curvature to the rib 24 but the blade 14 does not extend to the tip 28 as is more clearly seen in FIG. 2 of the drawings. The recessed portion 22 extends to the tip 28 and has a curved edge surface 29 leading from the tip 28 to cross and thus expose the blade cutting edge 30. As shown in FIG. 3 of the drawings, the face of the recessed portion 22 opposite the blade 14 is bevelled to clear a path to the blade cutting edge 30. Beyond the blade cutting edge 30 the edge surface again extends above the blade 14 to end at a blade guard 32 which extends upwardly of the body 12.

The blade 14 comprises a curved leading end 34, the inside edge of which forms the blade cutting edge 30, and a longer retaining portion 36 shaped to fit snugly within the recessed portion 22 of the head 20. The retaining portion 36 is slotted 38 to engage the retainer 16 which has a planer face 40 for abutting the blade and a curved outer face 42. Two pegs 44, 6 extend from the planer face 40 through the slot 38 in the retaining portion 36 of the blade to form an interference fit with two apertures 48, 50 provided in the recessed portion 42. The peg 44 located nearest to the tip 28 is of smaller diameter than the other peg 46 and the slot 38 is correspondingly narrower towards the curved leading end 36 to ensure that the blade 14 is securely located.

Figure 5:
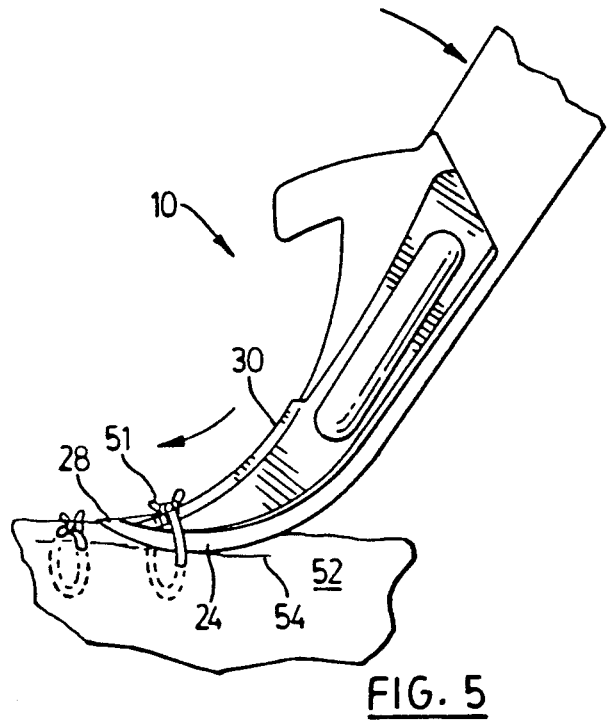
Figure 6:
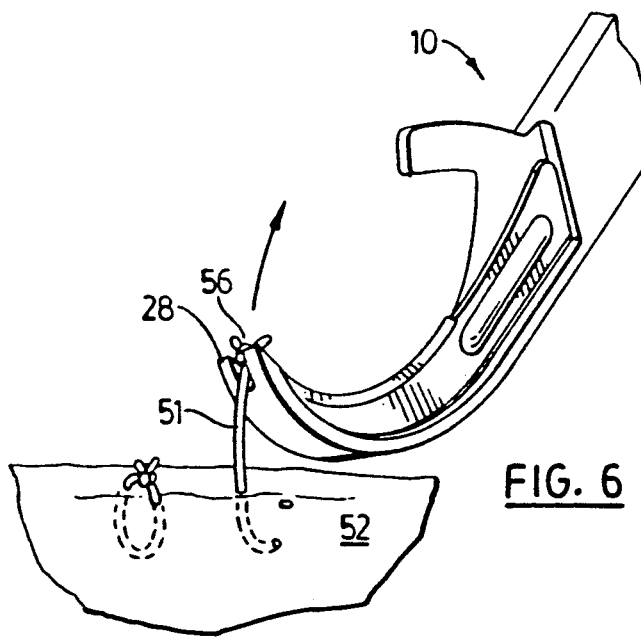

The use of the device 10 will now be described with reference to FIGS. 4 to 6 which illustrates steps in the removal of a suture. A user first inserts the forked tip 28 below a suture in the skin of a patient 52 at a healed wound 54, as shown in FIG. 4, to lift the suture from the skin. Then, by pushing and rotating the leading end of the device 10 forwards, as shown in FIG. 5, the suture 59 rides over the tip and onto the cutting edge 30. After the suture has been cut, the forked tip 28 is hooked around the knot 56 in the suture 51 and the cut suture 51 is easily pulled from the skin. The blade guard 32 ensures that the user's thumb, or other part of the hand, should not accidentally slip down onto the blade 14.

During the suture removing operation, only the outer face of the rib 24, and perhaps, the tip 28, contacts the skin of the patient. The only portion of the blade 16 which is exposed is the cutting edge 30, and this is located within the head 20 such that accidental injury to the patient is most unlikely.

Also, as the device 10 is light and compact medical staff can carry several individual sterile packs each containing one of the devices so that when, for example a doctor encounters a patient who requires a suture removed, the doctor can simply open one of the packs and remove the suture. The used devices may be discarded or sterilized and reused.

It should be noted that the device described above is merely exemplary and various modifications and improvements may be made without departing from the scope of the invention. For clarity of description the handle 18 has been shown as a plain molding, however, to provide a better grip on the handle, ribs or roughened portions may be provided, particularly adjacent the head 20 where a doctor would be likely to grip the device.

I claim:

1. A suture removing device comprising a body having a handle portion, a head portion and a cutting edge provided in the head portion, the head portion have a tapered leading end with a forked tip and a surface extending rearwardly of the tip to the cutting edge, wherein the cutting edge extends in a direction longitudinally of the device and the forked tip comprises a pair of prongs spaced in a direction transverse to said longitudinal direction, wherein said tapered leading end of the head portion is shaped to permit insertion thereof between a suture and a patient's skin to cause the suture to ride along said surface extending rearwardly of the tip to the cutting edge for cutting of the suture, and wherein said prongs are spaced to permit the tip to be hooked around a knot in the suture with a severed portion of the suture between said prongs, for pulling the suture from the skin.

2. A suture removing device as claimed in claim 1, in which the head portion is provided with a skin contacting surface extending rearwardly of the tip on the opposite side of the leading end from the surface extending rearwardly of the tip to the cutting edge.

3. A suture removing device as claimed in claim 2, in which the skin contacting surface is convex.

4. A suture removing device as claimed in claim 3, in which the cutting edge is formed on one edge of a detachable blade and the head portion is recessed to receive the blade, a retaining means being provided to retain the blade on the head portion.

5. A suture removing device as claimed in claim 4, in which the skin contacting surface is formed on a rib extending from the handle portion to the tip.

6. A suture removing device as claimed in claim 4, in which the surface of the leading end extending rearwardly of the tip to the cutting edge continues below the cutting edge to assist in locating the blade and is bevelled to clear the cutting edge.

7. A suture removing device as claimed in claim 4, in which the retaining means is in the form of a retaining member having a surface for abutting the blade and projections for engaging corresponding apertures in the blade and corresponding apertures in the leading end of the head portion.

8. A suture removing device as claimed in claim 1, in which the handle portion is elongate.

9. A suture removing device as claimed in claim 4, 7 or 8, in which a cutting edge guard extends from the head portion intermediate the cutting edge and the handle portion.

* * * * *